(12) United States Patent
Bender et al.

(10) Patent No.: US 8,138,171 B2
(45) Date of Patent: Mar. 20, 2012

(54) DIOXOLANE AND DIOXOLANONE FUSED INDOLOBENZADIAZEPINE HCV NS5B INHIBITORS

(75) Inventors: John A. Bender, Middletown, CT (US); Zhong Yang, Southington, CT (US); John F. Kadow, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/922,927

(22) PCT Filed: Mar. 26, 2009

(86) PCT No.: PCT/US2009/038441
§ 371 (c)(1),
(2), (4) Date: Sep. 16, 2010

(87) PCT Pub. No.: WO2009/120890
PCT Pub. Date: Oct. 1, 2009

(65) Prior Publication Data
US 2011/0020277 A1    Jan. 27, 2011

Related U.S. Application Data

(60) Provisional application No. 61/039,967, filed on Mar. 27, 2008.

(51) Int. Cl.
*A61P 31/18* (2006.01)
*A61K 31/407* (2006.01)
*C07D 491/056* (2006.01)

(52) U.S. Cl. .................................. 514/214.01; 540/576

(58) Field of Classification Search .............. 514/214.01; 540/576
See application file for complete search history.

(56) References Cited

U.S. PATENT DOCUMENTS

| | | |
|---|---|---|
| 7,153,848 B2 | 12/2006 | Hudyma et al. |
| 7,348,425 B2 | 3/2008 | Hudyma et al. |
| 7,399,758 B2 | 7/2008 | Meanwell et al. |
| 7,452,876 B2 | 11/2008 | Yeung et al. |
| 7,456,165 B2 | 11/2008 | Bergstrom et al. |
| 7,456,166 B2 | 11/2008 | Bender et al. |
| 7,456,167 B2 | 11/2008 | Bergstrom |
| 7,473,688 B2 | 1/2009 | Bergstrom et al. |
| 7,485,633 B2 | 2/2009 | Meanwell et al. |
| 7,517,872 B2 | 4/2009 | Nickel et al. |
| 7,521,441 B2 | 4/2009 | Gentles et al. |
| 7,521,442 B2 | 4/2009 | Gentles et al. |
| 7,521,443 B2 | 4/2009 | Bender et al. |
| 7,521,444 B2 | 4/2009 | Bender et al. |
| 7,538,102 B2 | 5/2009 | Yeung et al. |
| 7,538,103 B2 | 5/2009 | Hewawasam et al. |
| 7,541,351 B2 | 6/2009 | Bender et al. |
| 7,541,353 B2 | 6/2009 | Gentles et al. |
| 7,547,690 B2 | 6/2009 | Gentles et al. |
| 7,998,951 B2 | 8/2011 | Yeung et al. |
| 2009/0018163 A1 | 1/2009 | Schmitz et al. |
| 2009/0130056 A1 | 5/2009 | Bender et al. |
| 2009/0130057 A1 | 5/2009 | Hewawasam et al. |
| 2010/0216774 A1 | 8/2010 | Bender et al. |
| 2011/0020275 A1 | 1/2011 | Yeung et al. |

FOREIGN PATENT DOCUMENTS

| | | |
|---|---|---|
| WO | WO 2005/080399 | 9/2005 |
| WO | WO 2006/046030 | 5/2006 |
| WO | WO 2006/046039 | 5/2006 |
| WO | WO 2007/029029 | 3/2007 |
| WO | WO 2007/129119 | 11/2007 |

*Primary Examiner* — Brenda Coleman
(74) *Attorney, Agent, or Firm* — James Epperson

(57) ABSTRACT

The disclosure provides compounds of formula I, including their salts, as well as compositions and methods of using the compounds. The compounds have activity against hepatitis C virus (HCV) and are useful in treating those infected with HCV. I.

12 Claims, No Drawings

DIOXOLANE AND DIOXOLANONE FUSED INDOLOBENZADIAZEPINE HCV NS5B INHIBITORS

CROSS-REFERENCE TO RELATED APPLICATIONS

This application claims the benefit of U.S. provisional application Ser. No. 61/039,967 filed Mar. 27, 2008.

BACKGROUND OF THE INVENTION

The disclosure generally relates to the novel compounds of formula I, including their salts, which have activity against hepatitis C virus (HCV) and are useful in treating those infected with HCV. The disclosure also relates to compositions and methods of using these compounds.

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. N. Engl. J. Med. 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., Journal of Virology 2002, 3482-3492; and Defrancesco and Rice, Clinics in Liver Disease 2003, 7, 211-242.

Currently, the most effective HCV therapy employs a combination of alpha-interferon and ribavirin, leading to sustained efficacy in 40% of patients (Poynard, T. et al. Lancet 1998, 352, 1426-1432). Recent clinical results demonstrate that pegylated alpha-interferon is superior to unmodified alpha-interferon as monotherapy (Zeuzem, S. et al. N. Engl. J. Med. 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

The invention provides technical advantages, for example, the compounds are novel and are effective against hepatitis C. Additionally, the compounds provide advantages for pharmaceutical uses, for example, with regard to one or more of their mechanism of action, binding, inhibition efficacy, target selectivity, solubility, safety profiles, or bioavailability.

HCV NS5B inhibitors have been disclosed in U.S. Pat. No. 7,399,758.

DESCRIPTION OF THE INVENTION

The invention encompasses compounds of formula I, including pharmaceutically acceptable salts, and compositions and methods of treatment using these compounds.

One aspect of the invention is a compound of formula I

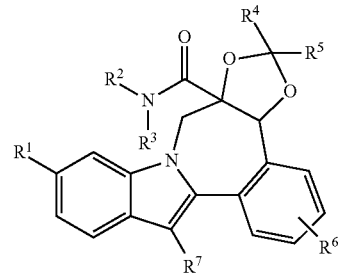

where:
$R^1$ is $CO_2R^8$ or $CONR^9R^{10}$;
$R^2$ is hydrogen, alkyl, aminoalkyl, alkylaminoalkyl, or dialkylaminoalkyl;
$R^3$ is hydrogen, alkyl, aminoalkyl, alkylaminoalkyl, or dialkylaminoalkyl;
or $NR^2R^3$ taken together is azetidinyl, pyrrolidinyl, piperidinyl, piperazinyl, N-(alkyl)piperazinyl, morpholinyl, thiomorpholinyl, homopiperidinyl, or homomorpholinyl, and is substituted with 0-3 alkyl substituents;
or $NR^2R^3$ taken together is

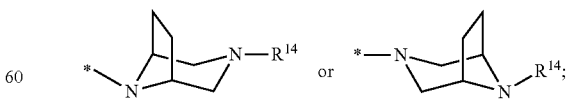

$R^4$ is hydrogen or alkyl;
$R^5$ is hydrogen or alkyl;
or $R^4$ and $R^5$ taken together is oxo;
$R^6$ is hydrogen, halo, alkyl, alkenyl, hydroxy, benzyloxy, or alkoxy;

$R^7$ is cycloalkyl;
$R^8$ is hydrogen or alkyl;
$R^9$ is hydrogen, alkyl, alkylSO$_2$, cycloalkylSO$_2$, haloalkylSO$_2$, $(R^{11})(R^{12})NSO_2$, or $(R^{13})SO_2$;
$R^{10}$ is hydrogen or alkyl;
$R^{11}$ is hydrogen or alkyl;
$R^{12}$ is hydrogen or alkyl;
$R^{13}$ is azetidinyl, pyrrolidinyl, piperidinyl, piperazinyl, N-(alkyl)piperazinyl, morpholinyl, thiomorpholinyl, homopiperidinyl, or homomorpholinyl; and
$R^{14}$ is hydrogen, alkyl, cycloalkyl, (cycloalkyl)alkyl, alkylcarbonyl, cycloalkylcarbonyl, haloalkylcarbonyl, alkoxycarbonyl, alkylSO$_2$, cycloalkylSO$_2$, haloalkylSO$_2$, aminocarbonyl, (alkylamino)carbonyl, (dialkylamino)carbonyl, benzyl, benzyloxycarbonyl, or pyridinyl;
or a pharmaceutically acceptable salt thereof.

Another aspect of the invention is a compound of formula I where $R^1$ is CONR$^9$R$^{10}$; $R^2$ is dialkylaminoalkyl; $R^3$ is alkyl; or NR$^2$R$^3$ taken together is morpholinyl substituted with 2 alkyl substituents or NR$^2$R$^3$ taken together is

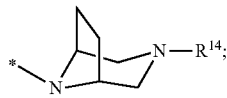

$R^4$ is hydrogen or alkyl; $R^5$ is hydrogen or alkyl; or $R^4$ and $R^5$ taken together is oxo; $R^6$ is alkoxy; $R^7$ is cycloalkyl; $R^9$ is $(R^{11})(R^{12})NSO_2$; $R^{11}$ is alkyl; $R^{12}$ is alkyl; and $R^{14}$ is alkyl; or a pharmaceutically acceptable salt thereof.

Another aspect of the invention is a compound of formula I where $R^1$ CONHSO$_2$NMe$_2$; $R^2$ is dimethylaminoethyl; $R^3$ is methyl; or NR$^2$R$^3$ taken together is 3,5-dimethylmorpholinyl or NR$^2$R$^3$ taken together is 3-methyl-3,8-diazabicyclo[3.2.1] oct-8-yl; $R^4$ is hydrogen or methyl; $R^5$ is hydrogen or methyl; or $R^4$ and $R^5$ taken together is oxo; $R^6$ is methoxy; $R^7$ is cyclohexyl; or a pharmaceutically acceptable salt thereof.

Another aspect of the invention is a compound of formula I where $R^1$ is CONR$^9$R$^{10}$; $R^9$ is alkylSO$_2$, cycloalkylSO$_2$, haloalkylSO$_2$, $(R^{11})(R^{12})NSO_2$, or $(R^{13})SO_2$; and $R^{10}$ is hydrogen.

Another aspect of the invention is a compound of formula I where $R^6$ is hydrogen.

Another aspect of the invention is a compound of formula I where $R^6$ is methoxy.

Another aspect of the invention is a compound of formula I where $R^7$ is cyclohexyl.

Another aspect of the invention is a compound of formula I where $R^9$ is $(R^{11})(R^{12})NSO_2$ or $(R^{13})SO_2$.

For a compound of Formula I, the scope of any instance of a variable substituent, including $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$, can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. "Haloalkyl" and "haloalkoxy" include all halogenated isomers from monohalo to perhalo. Terms with a hydrocarbon moiety (e.g. alkoxy) include straight and branched isomers for the hydrocarbon portion. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (see, for example, the compounds below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art.

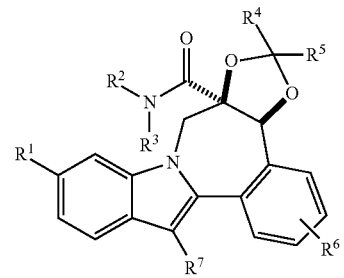

Synthetic Methods

The compounds may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for $CF_3(CF_2)_3SO_2$—; and "TMOF" for trimethylorthoformate.

Some of the compounds can be synthesized by the methods illustrated in Scheme 1. Hydrolysis of known 5H-indolo[2,1-a][2]benzazepine esters with nucleophilic hydroxides can generate the corresponding carboxylic acid which can then be coupled with a variety of primary or secondary amines to form the corresponding amides using one of the many known standard amidation conditions. The resulting unsaturated amide can be subjected to dihyroxylation conditions, typically employing catalytic osmium tetroxide or ruthenium(III) chloride with stoichiometric quantities of a co-oxidant to form cis-diols compounds. The cis-diols can then be cyclized to form 1,3-dioxolane compounds under acid conditions using ketones, aldehydes or enol ethers as reactants. Alternatively, the 1,3 dioxolane (or dioxolanone) compounds can be formed under basic conditions using reactants that have two leaving groups on the same carbon which is susceptible to nucleophilic attack.

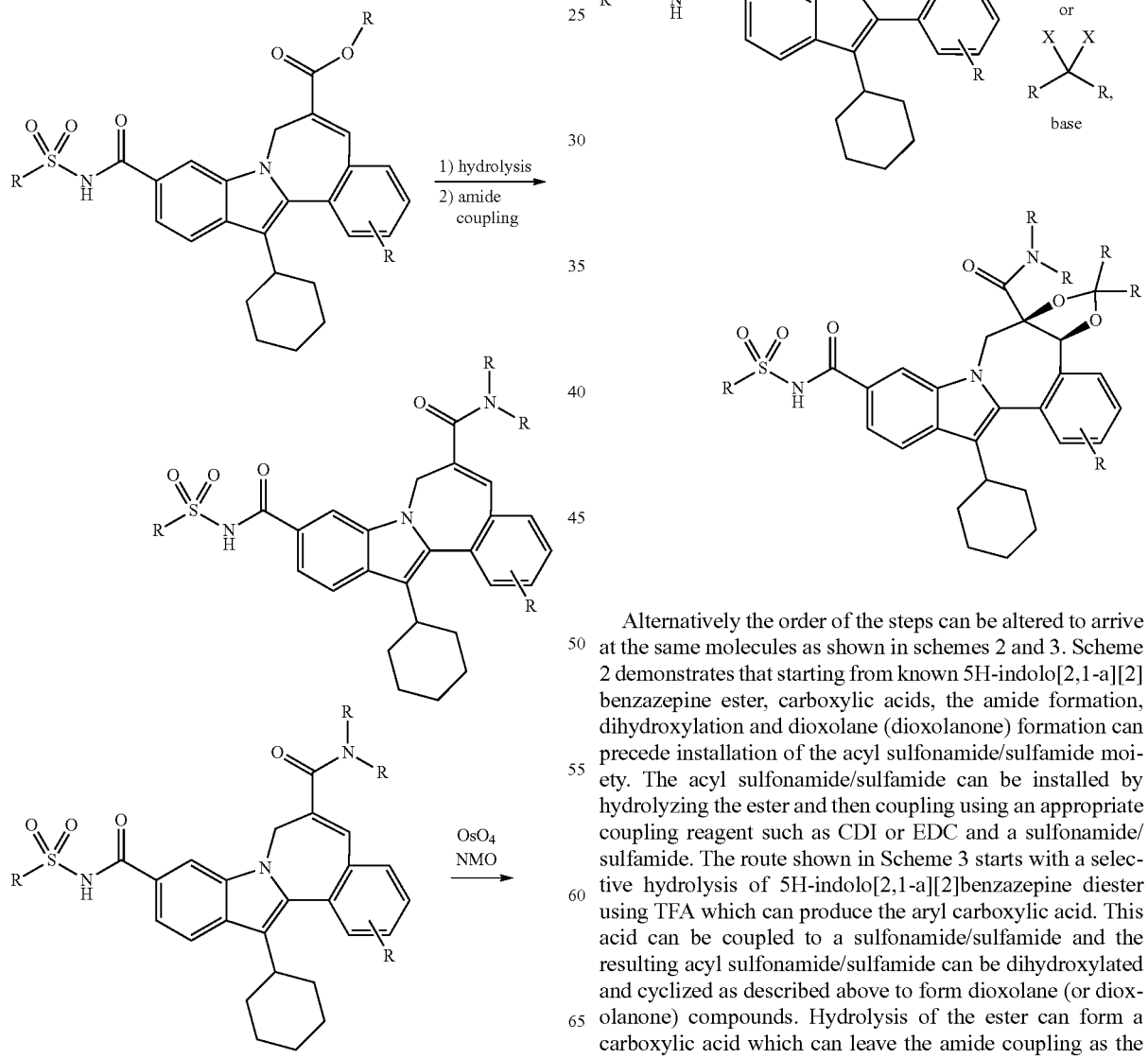

Alternatively the order of the steps can be altered to arrive at the same molecules as shown in schemes 2 and 3. Scheme 2 demonstrates that starting from known 5H-indolo[2,1-a][2] benzazepine ester, carboxylic acids, the amide formation, dihydroxylation and dioxolane (dioxolanone) formation can precede installation of the acyl sulfonamide/sulfamide moiety. The acyl sulfonamide/sulfamide can be installed by hydrolyzing the ester and then coupling using an appropriate coupling reagent such as CDI or EDC and a sulfonamide/sulfamide. The route shown in Scheme 3 starts with a selective hydrolysis of 5H-indolo[2,1-a][2]benzazepine diester using TFA which can produce the aryl carboxylic acid. This acid can be coupled to a sulfonamide/sulfamide and the resulting acyl sulfonamide/sulfamide can be dihydroxylated and cyclized as described above to form dioxolane (or dioxolanone) compounds. Hydrolysis of the ester can form a carboxylic acid which can leave the amide coupling as the final step.

Scheme 2.
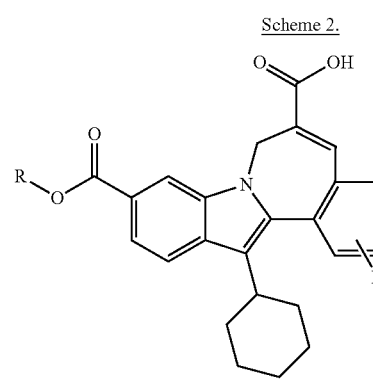
1) amide coupling
2) OsO$_4$ NMO
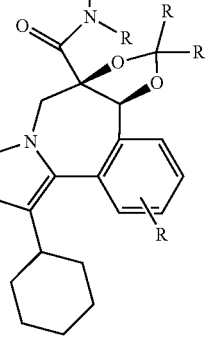
1) hydrolysis
2) sulfonamide or sulfamide coupling
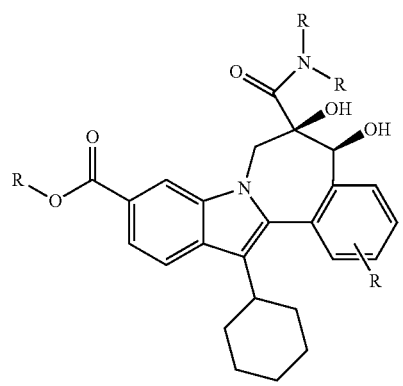
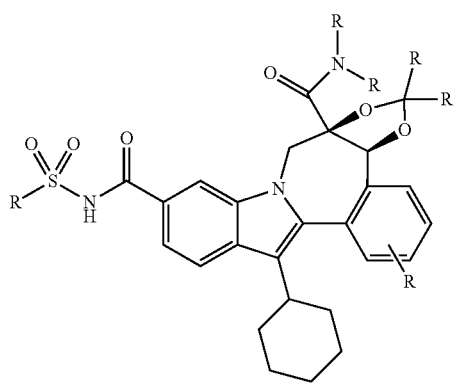
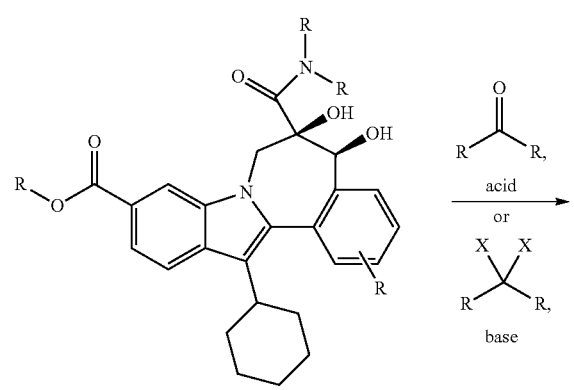
acid or
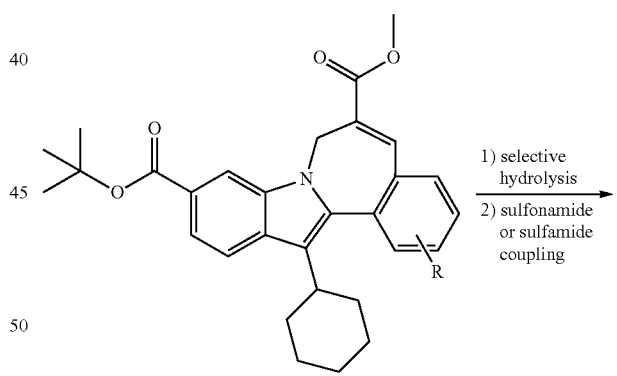
Scheme 3.
1) selective hydrolysis
2) sulfonamide or sulfamide coupling
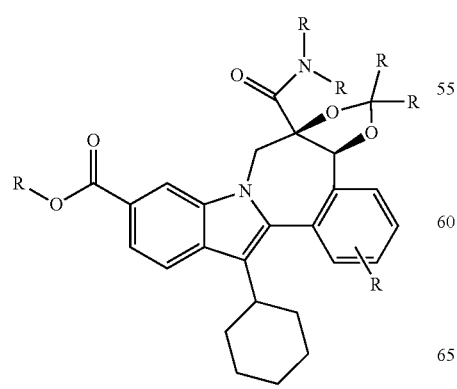
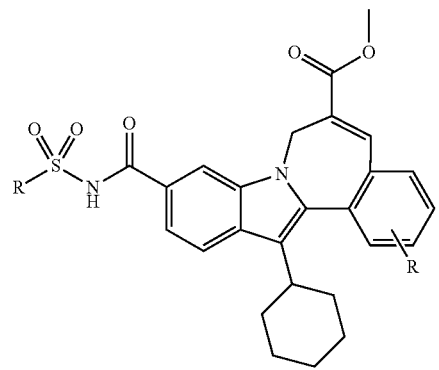

-continued

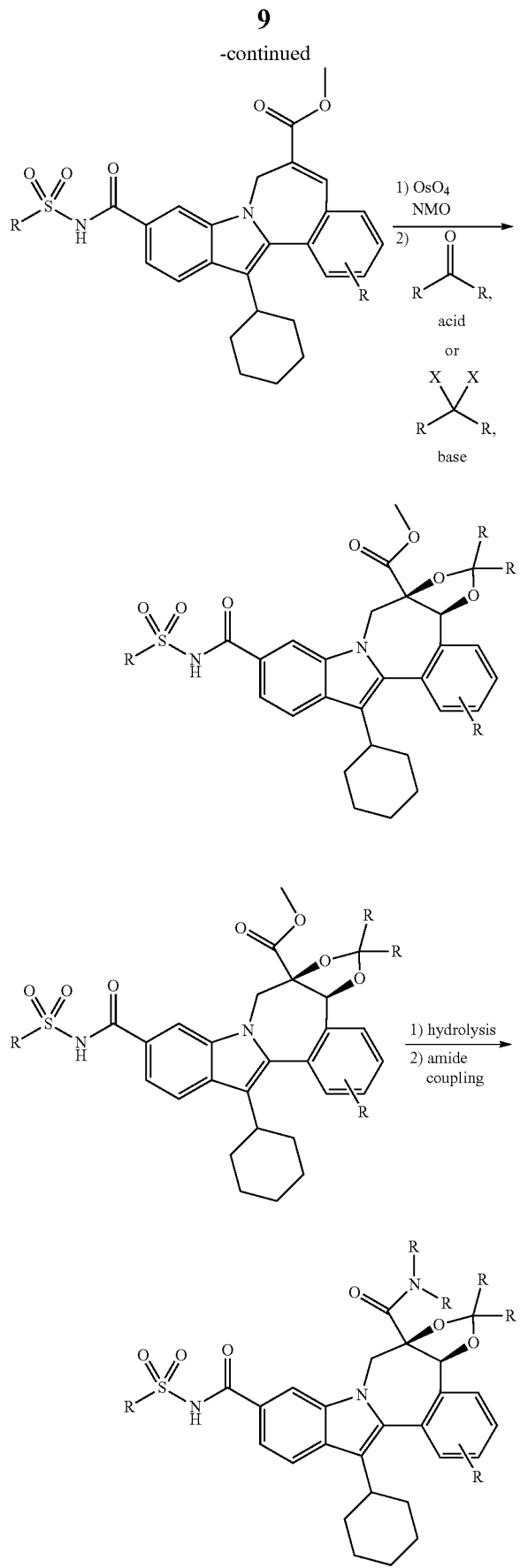

Biological Methods

The compounds demonstrated activity against HCV NS5B as determined in the following HCV RdRp assays.

HCV NS5B RdRp cloning, expression, and purification. The cDNA encoding the NS5B protein of HCV, genotype 1b, was cloned into the pET21a expression vector. The protein was expressed with an 18 amino acid C-terminal truncation to enhance the solubility. The E. coli competent cell line BL21 (DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 µg/ml and the cells were grown overnight at 20° C.

Cell pellets (3 L) were lysed for purification to yield 15-24 rags of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/ml lysozyme, 10 mM MgCl2, 15 ug/ml deoxyribonuclease I, and Complete™ protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 1 hr at 4° C. and filtered through a 0.2 µm filter unit (Corning).

The protein was purified using three sequential chromatography steps: Heparin sepharose CL-6B, polyU sepharose 4B, and Hitrap SP sepharose (Pharmacia). The chromatography buffers were identical to the lysis buffer but contained no lysozyme, deoxyribonuclease I, MgCl2 or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

Standard HCV NS5B RdRp enzyme assay. HCV RdRp genotype 1b assays were run in a final volume of 60 µl in 96 well plates (Costar 3912). The assay buffer is composed of 20 mM Hepes, pH 7.5, 2.5 mM KCl, 2.5 mM MgCl2, 1 mM DTT, 1.6 U RNAse inhibitor (Promega N2515), 0.1 mg/ml BSA (Promega R3961), and 2% glycerol. All compounds were serially diluted (3-fold) in DMSO and diluted further in water such that the final concentration of DMSO in the assay was 2%. HCV RdRp genotype 1b enzyme was used at a final concentration of 28 nM. A polyA template was used at 6 nM, and a biotinylated oligo-dT12 primer was used at 180 nM final concentration. Template was obtained commercially (Amersham 27-4110). Biotinylated primer was prepared by Sigma Genosys. 3H-UTP was used at 0.6 µCi (0.29 µM total UTP). Reactions were initiated by the addition of enzyme, incubated at 30° C. for 60 min, and stopped by adding 25 µl of 50 mM EDTA containing SPA beads (4 µg/µl, Amersham RPNQ 0007). Plates were read on a Packard Top Count NXT after >1 hr incubation at room temperature.

Modified HCV NS5B RdRp enzyme assay. A modified enzyme assay was performed essentially as described for the standard enzyme assay except for the following: The biotinylated oligo dT12 primer was precaptured on streptavidin-coated SPA beads by mixing primer and beads in assay buffer and incubating at room temperature for one hour. Unbound primer was removed after centrifugation. The primer-bound beads were resuspended in 20 mM Hepes buffer, pH 7.5 and used in the assay at final concentrations of 20 nM primer and 0.67 μg/μl beads. Order of addition in the assay: enzyme (14 nM) was added to diluted compound followed by the addition of a mixture of template (0.2 nM), 3H-UTP (0.6 μCi, 0.29 μM), and primer-bound beads, to initiate the reaction; concentrations given are final. Reactions were allowed to proceed for 4 hours at 30° C.

$IC_{50}$ values for compounds were determined using seven different [1]. $IC_{50}$ values were calculated from the inhibition using the formula $y=A+((B-A)/(1+((C/x)^D)))$.

FRET Assay Preparation. To perform the HCV FRET screening assay, 96-well cell culture plates were used. The FRET peptide (Anaspec, Inc.) (Taliani et al., *Anal. Biochem.* 1996, 240, 60-67) contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent. The assay reagent was made as follows: 5× cell Luciferase cell culture lysis reagent from Promega (#E153A) diluted to 1× with $dH_2O$, NaCl added to 150 mM final, the FRET peptide diluted to 20 uM final from a 2 mM stock.

To prepare plates, HCV replicon cells, with or without a *Renilla* luciferase reporter gene, were trypsinized and placed into each well of a 96-well plate with titrated test compounds added in columns 3 through 12; columns 1 and 2 contained a control compound (HCV protease inhibitor), and the bottom row contained cells without compound. The plates were then placed in a $CO_2$ incubator at 37° C.

Assays. Subsequent to addition of the test compounds described above (FRET Assay Preparation), at various times the plate was removed and Alamar blue solution (Trek Diagnostics, #00-100) was added per well as a measure of cellular toxicity, After reading in a Cytoflour 4000 instrument (PE Biosystems), plates were rinsed with PBS and then used for FRET assay by the addition of 30 ul of the FRET peptide assay reagent described above (FRET Assay Preparation) per well. The plate was then placed into the Cytoflour 4000 instrument which had been set to 340 excite/490 emission, automatic mode for 20 cycles and the plate read in a kinetic mode. Typically, the signal to noise using an endpoint analysis after the reads was at least three-fold. Alternatively, after Alamar blue reading, plates were rinsed with PBS, 50 ul of DMEM (high glucose) without phenol red was added and plates were then used for luciferase assay using the Promega Dual-Glo Luciferase Assay System.

Compound analysis was determined by quantification of the relative HCV replicon inhibition and the relative cytotoxicity values. To calculate cytoxicity values, the average Alamar Blue fluorescence signals from the control wells were set as 100% non-toxic. The individual signals in each of the compound test wells were then divided by the average control signal and multiplied by 100% to determine percent cytotoxicity. To calculate the HCV replicon inhibition values, an average background value was obtained from the two wells containing the highest amount of HCV protease inhibitor at the end of the assay period. These numbers were similar to those obtained from naive Huh-7 cells.

The background numbers were then subtracted from the average signal obtained from the control wells and this number was used as 100% activity. The individual signals in each of the compound test wells were then divided by the averaged control values after background subtraction and multiplied by 100% to determine percent activity. $EC_{50}$ values for a protease inhibitor titration were calculated as the concentration which caused a 50% reduction in FRET or luciferase activity. The two numbers generated for the compound plate, percent cytoxicity and percent activity were used to determine compounds of interest for further analysis.

Representative data for compounds are reported in Table 1.

TABLE 1

| Example | Structure | $IC_{50}$ (uM) | $EC_{50}$ (uM) |
|---------|-----------|----------------|----------------|
| 1 | 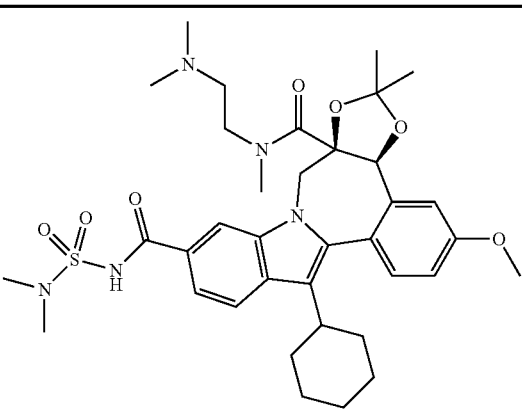 | 0.17 | 0.13 |

TABLE 1-continued

| Example | Structure | IC$_{50}$ (uM) | EC$_{50}$ (uM) |
|---|---|---|---|
| 2 | 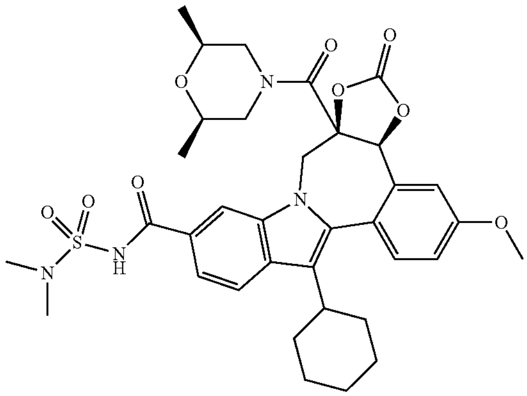 | 0.033 | 0.059 |
| 3 | 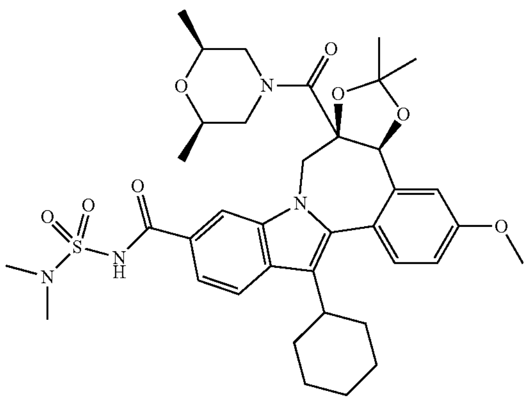 | 0.11 | 0.17 |
| 4 | 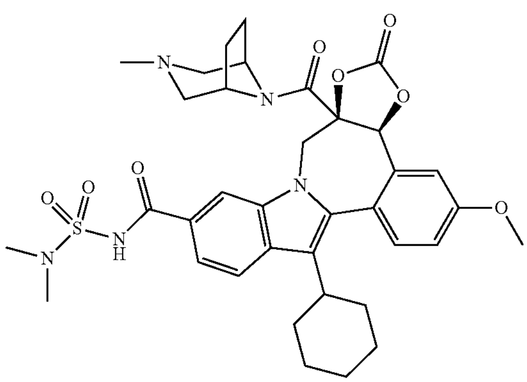 | 0.091 | 0.10 |
| 5 | 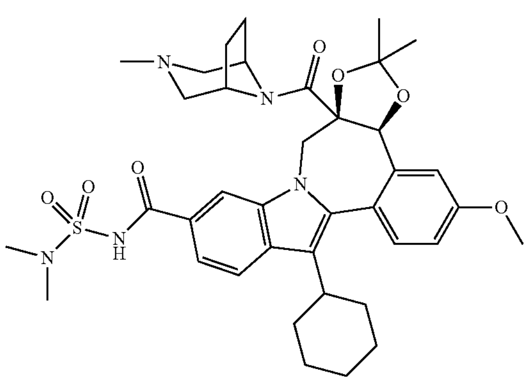 | 0.59 | 0.14 |

TABLE 1-continued

| Example | Structure | IC$_{50}$ (uM) | EC$_{50}$ (uM) |
|---------|-----------|----------------|----------------|
| 6 | 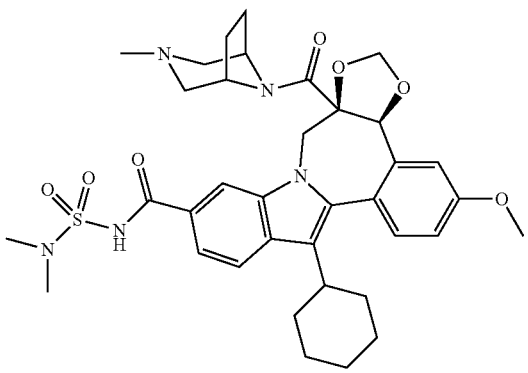 | 0.43 | 0.14 |

A > 0.5 μM;
B 0.02 μM-0.5 μM;
C < 0.02 μM but an exact value was not determined;
IC$_{50}$ values were determined using the preincubation protocol.
EC$_{50}$ values were determined using the FRET assay.

Pharmaceutical Compositions and Methods of Treatment

The compounds demonstrate activity against HCV NS5B and can be useful in treating HCV and HCV infection. Therefore, another aspect of the invention is a composition comprising a compound of formula I, or a pharmaceutically acceptable salt thereof, and a pharmaceutically acceptable carrier.

Another aspect of the invention is the use of a compound of formula I in the manufacture of a medicament for the treatment of hepatitis C.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophosphate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound of formula I, or a pharmaceutically acceptable salt thereof, a pharmaceutically acceptable carrier, and an interferon and ribavirin.

Another aspect of the invention is a method of inhibiting the function of the HCV replicon comprising contacting the HCV replicon with a compound of formula I or a pharmaceutically acceptable salt thereof.

Another aspect of the invention is a method of inhibiting the function of the HCV NS5B protein comprising contacting the HCV NS5B protein with a compound of formula I or a pharmaceutically acceptable salt thereof.

Another aspect of the invention is a method of treating an HCV infection in a patient comprising administering to the patient a therapeutically effective amount of a compound of formula I or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound of formula I, or a pharmaceutically acceptable salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophosphate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection, In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 2.

TABLE 2

| Brand Name | Type of Inhibitor or Target | Source Company |
|---|---|---|
| Omega IFN | IFN-ω | BioMedicines Inc., Emeryville, CA |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon-α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/SciClone Pharmaceuticals Inc, San Mateo, CA |
| Levovirin | IMPDH inhibitor | Ribapharm Inc., Costa Mesa, CA |
| Viramidine | IMPDH inhibitor | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/Ribavirin | PEGylated IFN-α2b/ribavirin | Schering-Plough Corporation, Kenilworth, NJ |
| Zadazim | immune modulator | SciClone Pharmaceuticals Inc., San Mateo, CA |

TABLE 2-continued

| Brand Name | Type of Inhibitor or Target | Source Company |
| --- | --- | --- |
| Rebif | IFN-β1a | Serono, Geneva, Switzerland |
| IFN-β and EMZ701 | IFN-β and EMZ701 | Transition Therapeutics Inc., Ontario, Canada |
| T67 | β-tubulin inhibitor | Tularik Inc., South San Francisco, CA |
| VX-497 | IMPDH inhibitor | Vertex Pharmaceuticals Inc., Cambridge, MA |
| VX-950/ LY-570310 | serine protease inhibitor | Vertex Pharmaceuticals Inc., Cambridge, MA/ Eli Lilly and Co. Inc., Indianapolis, IN |
| Omniferon | natural IFN-α | Viragen Inc., Plantation, FL |
| XTL-002 | monoclonal antibody | XTL Biopharmaceuticals Ltd., Rehovot, Isreal |

DESCRIPTION OF SPECIFIC EMBODIMENTS

| LCMS data: | |
| --- | --- |
| Stop time: | Gradient time + 1 minute |
| Starting conc: | 0% B unless otherwise noted |
| Eluent A: | 5% $CH_3CN$/95% $H_2O$ with 10 mM $NH_4OAc$ (for columns A, D, E and F) |
| | 10% MeOH/90% $H_2O$ with 0.1% TFA (for columns B and C) |
| Eluent B: | 95% $CH_3CN$/5% $H_2O$ with 10 mM $NH_4OAc$ (for columns A, D, E and F) |
| | 90% MeOH/10% $H_2O$ with 0.1% TFA (for columns B and C) |
| Column A: | Phenomenex 10μ 4.6 × 50 mm C18 |
| Column B: | Phenomenex C18 10μ 3.0 × 50 mm |
| Column C: | Phenomenex 4.6 × 50 mm C18 10μ |
| Column D: | Phenomenex Lina C18 5μ 3.0 × 50 mm |
| Column E: | Phenomenex 5μ 4.6 × 50 mm C18 |
| Column F: | Phenomenex 10μ C18 4.6 × 30 mm |
| Preparative HPLC data: | |
| Gradient: | Linear over 20 min. unless otherwise noted |
| Starting conc: | 15% B unless otherwise noted |
| Ending conc: | 100% B |
| Eluent A: | 5% $CH_3CN$/95% $H_2O$ with 10 mM $NH_4OAc$ |
| Eluent B: | 95% $CH_3CN$/5% $H_2O$ with 10 mM $NH_4OAc$ |
| Column: | Sunfire Prep $C_{18}$ OBD 5μ 30 × 100 mm |

The preparation of the following starting materials can be found in US 2007060565.
1) 10-(1,1-dimethylethyl)-6-methyl-13-cyclohexyl-3-(methyloxy)-5H-indolo[2,1-a][2]benzazepine-6,10-dicarboxylate
2) 7H-Indolo[2,1-a][2]benzazepine-6-carboxylic acid, 13-cyclohexyl-10-[[[(dimethylamino)sulfonyl]amino]carbonyl]-3-methoxy-, methyl ester The preparation of the following starting materials can be found in WO 2007033175.
3) 7H-Indolo[2,1-a][2]benzazepine-6-carboxylic acid, 13-cyclohexyl-10-[[[(dimethylamino)sulfonyl]amino]carbonyl]-3-methoxy-, carboxylic acid The preparation of the following starting materials can be found in US 2006166964.
4) 13-cyclohexyl-N-((dimethylamino)sulfonyl)-6-(((2S,6R)-2,6-dimethyl-4-morpholinyl)carbonyl)-3-(methyloxy)-6,7-dihydro-7H-indolo[2,1-a][2]benzazepine-10-carboxamide

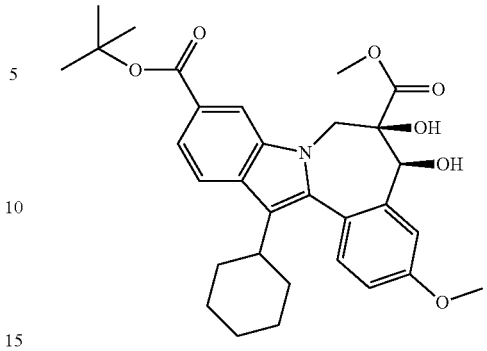

Intermediate 1

10-(1,1-Dimethylethyl) 6-methyl rac-(5R,6S)-13-cyclohexyl-5,6-dihydroxy-3-(methyloxy)-6,7-dihydro-5H-indolo[2,1-a][2]benzazepine-6,10-dicarboxylate. To a slurry of 10-(1,1-dimethylethyl)-6-methyl-13-cyclohexyl-3-(methyloxy)-7H-indolo[2,1-a][2]benzazepine-6,10-dicarboxylate (400 mg, 0.80 mmol) and 4-methylmorpholine N-oxide (234 mg, 2.0 mmol) in THF (5 mL) was added $H_2O$ (0.20 mL) and $OsO_4$ (0.20 mL of a 2.5% w/w solution of $OsO_4$ in t-BuOH). The reaction was stirred at rt for 2 h, quenched with sat $Na_2S_2O_3$ (aq.) (~5 mL) and stirred 1 h. The layers were separated, and the aqueous layer was extracted with THF (2×5 mL). The combined organics were concentrated and the residue was dissolved into DMF (2 mL) and treated with $H_2O$ (~4 mL). The solids were collected by filtration to yield 10-(1,1-dimethylethyl) 6-methyl rac-(5R,6S)-13-cyclohexyl-5,6-dihydroxy-3-(methyloxy)-6,7-dihydro-5H-indolo[2,1-a][2]benzazepine-6,10-dicarboxylate (413 mg, 0.77 mmol, 96%) as a yellow solid which was used without further purification. $^1$HNMR (300 MHz, $CD_3OD$) δ 1.22-2.19 (m, 10H), 1.65 (s, 9H), 2.87-3.12 (m, 2H), 3.53 (d, J=15.0 Hz, 1H), 3.68 (s, 3H), 3.93 (s, 3H), 4.63 (d, J=15.0 Hz, 1H), 7.05 (dd, J=8.4, 2.9 Hz, 1H), 7.36-7.43 (m, 2H), 7.65 (dd, J=8.4, 1.1 Hz, 1H), 7.84 (d, J=8.4 Hz, 1H), 7.91 (br s, 1H). LCMS: m/e 536 (M+H)$^+$, ret time 3.11 min, column D, 4 minute gradient.

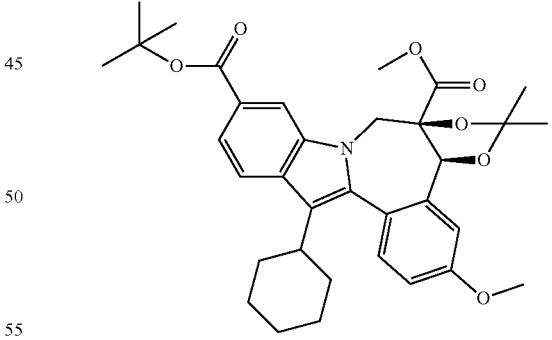

Intermediate 2

7-(1,1-Dimethylethyl) 3a-methyl rac-(3aR,14bS)-10-cyclohexyl-2,2-dimethyl-13-(methyloxy)-4H-[1,3]dioxolo[4,5-d]indolo[2,1-a][2]benzazepine-3a,7(14bH)-dicarboxylate. To a solution of 10-(1,1-dimethylethyl) 6-methyl rac-(5R,6S)-13-cyclohexyl-5,6-dihydroxy-3-(methyloxy)-6,7-dihydro-5H-indolo[2,1-a][2]benzazepine-6,10-dicarboxylate (30 mg, 0.056 mmol) in THF (1 mL) was added 2-methoxypropene (0.2 mL) and then TsOH monohydrate (5 mg). The reaction mixture was stirred overnight and then concentrated to dryness. The residue was dissolved into DMSO/MeOH and purified by preparative HPLC to yield 7-(1,1-dimethylethyl) 3a-methyl rac-(3aR,14bS)-10-cyclohexyl-2,2-dimethyl-13-

(methyloxy)-4H-[1,3]dioxolo[4,5-d]indolo[2,1-a][2]benzazepine-3a,7(14bH)-dicarboxylate (17 mg, 0.030 mmol, 53%) as a yellow solid. ¹H NMR (300 MHz, CDCl₃) δ 0.32 (s, 3H), 0.80-2.16 (m, 10H), 1.33 (s, 3H), 1.60 (s, 9H), 2.83-2.95 (m, 1H), 3.85 (s, 3H), 3.87 (s, 3H), 4.00 (d, J=14.8 Hz, 1H), 4.46 (d, J=14.8 Hz, 1H), 5.21 (s, 1H), 7.00 (d, J=2.6 Hz, 1H), 7.04 (dd, J=8.4, 2.6 Hz, 1H), 7.40 (d, J=8.4 Hz, 1H), 7.67 (dd, J=8.4, 1.1 Hz, 1H), 7.77 (d, J=8.4 Hz, 1H), 7.98 (br s, 1H). LCMS: m/e 576 (M+H)⁺, ret time 4.28 min, column A, 4 minute gradient.

Intermediate 3

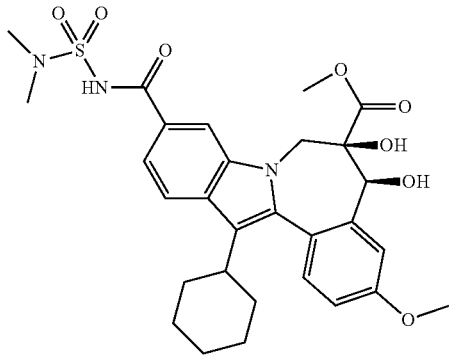

Methyl rac-(5R,6S)-13-cyclohexyl-10-((((dimethylamino)sulfanyl)amino)carbonyl)-5,6-dihydro-3-(methyloxy)-6,7-dihydro-5H-indolo[2,1-a][2]benzazepine-6-carboxylate. To a solution of 7H-indolo[2,1-a][2]benzazepine-6-carboxylic acid, 13-cyclohexyl-10-[[[(dimethylamino)sulfonyl]amino]carbonyl]-3-methoxy-, methyl ester (70 mg, 0.13 mmol) and 4-methylmorpholine N-oxide (37 mg, 0.32 mmol) in THF (1 mL) was added H₂O (0.10 mL) and OsO₄ (0.10 mL of a 2.5% w/w solution of OsO₄ in t-BuOH). The reaction was stirred at rt for 2 h, quenched with sat. Na₂S₂O₃ (aq.) (~1.5 mL) and stirred 1 h. The layers were separated, and the aqueous layer was extracted with THF (2×2 mL). The combined organics were concentrated and the residue was dissolved into DMF/MeOH (1:2, 3 mL), filtered and purified by preparative HPLC to yield methyl rac-(5R,6S)-13-cyclohexyl-10-((((dimethylamino)sulfonyl)amino)carbonyl)-5,6-dihydroxy-3-(methyloxy)-6,7-dihydro-5H-indolo[2,1-a][2]benzazepine-6-carboxylate (62 mg, 0.11 mmol, 83%) as a light yellow solid. ¹HNMR (300 MHz, d₆-DMSO) δ 1.07-2.10 (m, 10H), 2.80-2.92 (m, 1H), 2.90 (s, 6H), 3.31-3.39 (m, 1H), 3.57 (s, 3H), 3.86 (s, 3H), 4.65-4.74 (m, 2H), 5.56-5.60 (m, 1H), 5.74-5.80 (m, 1H), 7.07 (dd, J=8.4, 2.9 Hz, 1H), 7.26 (d, J=2.9 Hz, 1H), 7.36 (d, J=8.4 Hz, 1H), 7.63 (dd, J=8.4, 1.3 Hz, 1H), 7.87 (d, J=8.4 Hz, 1H), 8.36 (br s, 1H), 11.38 (s, 1H). LCMS: m/e 584 (M–H)⁻, ret time 1.86 min, column A, 4 minute gradient.

Intermediate 4

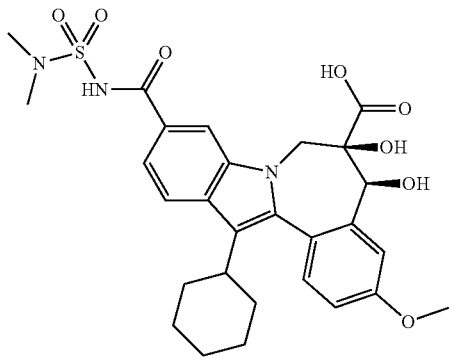

rac-(5R,6S)-13-Cyclohexyl-10-((((dimethylamino)sulfonyl)amino)carbonyl)-5,6-dihydroxy-3-(methyloxy)-6,7-dihydro-5H-indolo[2,1-a][2]benzazepine-6-carboxylic acid. To a solution of methyl rac-(5R,6S)-13-cyclohexyl-10-((((dimethylamino)sulfonyl)amino)carbonyl)-5,6-dihydroxy-3-(methyloxy)-6,7-dihydro-5H-indolo[2,1-a][2]benzazepine-6-carboxylate (57 mg, 0.10 mmol) in MeOH/THF (1:1, 2 mL) was added 1M NaOH aq. (0.5 mL). The reaction was sealed and heated at 80° C. for 20 min with microwave irradiation. The reaction was quenched with 1N HCl aq. (0.5 mL), diluted with H₂O and concentrated to remove the organic solvents. The resulting precipitates were collected by filtration and dried under vacuum to yield rac-(5R,6S)-13-cyclohexyl-10-((((dimethylamino)sulfonyl)amino)carbonyl)-5,6-dihydroxy-3-(methyloxy)-6,7-dihydro-5H-indolo[2,1-a][2]benzazepine-6-carboxylic acid (42 mg, 0.074 mmol, 73%) as a yellow solid. ¹HNMR (300 MHz, CD₃OD) δ 0.73-2.20 (m, 10H), 2.92-3.05 (m, 1H), 3.02 (s, 6H), 3.54 (d, J=14.8 Hz, 1H), 3.93 (s, 3H), 4.71 (d, J=14.8 Hz, 1H), 4.94 (s, 1H), 7.05 (dd, J=8.4, 2.6 Hz, 1H), 7.40 (d, J=2.6 Hz, 1H), 7.40 (d, J=8.4 Hz, 1H), 7.59 (dd, J=8.4, 1.5 Hz, 1H), 7.89 (d, J=8.4 Hz, 1H), 8.05 (d, J=1.5 Hz, 1H). LCMS: m/e 572 (M+H)⁺, ret time 3.34 min, column B, 4 minute gradient.

Intermediate 5

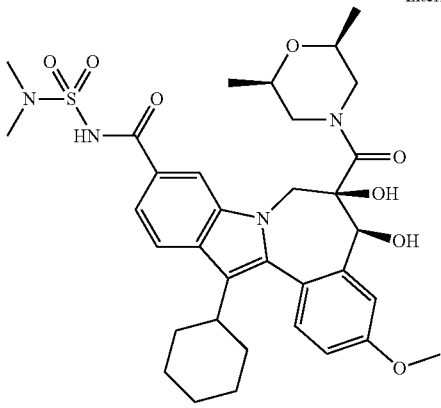

rac-(5R,6S)-13-Cyclohexyl-N-((dimethylamino)sulfonyl)-6-(((2S,6R)-2,6-dimethyl-4-morpholinyl)carbonyl)-5,6-dihydroxy-3-(methyloxy)-6,7-dihydro-5H-indolo[2,1-a][2]benzazepine-10-carboxamide. To a solution of 13-cyclohexyl-N-((dimethylamino)sulfonyl)-6-(((2S,6R)-2,6-dimethyl-4-morpholinyl)carbonyl)-3-(methyloxy)-6,7-dihydro-7H-indolo[2,1-a][2]benzazepine-10-carboxamide (500 mg, 0.79 mmol) and 4-methylmorpholine N-oxide (231 mg, 1.97 mmol) in THF/H₂O (10:1, 5.5 mL) was added OsO₄ (0.50 mL of a 2.5% w/w solution of OsO₄ in t-BuOH, 0.04 mmol). The reaction was stirred at rt for 18 h, quenched with sat. Na₂S₂O₃ (aq.) (~10 mL) and stirred 6 h. The layers were separated, and the aqueous layer was extracted with THF (2×20 mL). The combined organics were washed with sat. Na₂S₂O₃ (aq.) (~30 mL) and brine (30 mL) and concentrated. The residue was dissolved into DMF/MeOH (1:2, 15 mL), filtered and purified by preparative HPLC to yield rac-(5R,6S)-13-cyclohexyl-N-((dimethylamino)sulfonyl)-6-(((2S,6R)-2,6-dimethyl-4-morpholinyl)carbonyl)-5,6-dihydroxy-3-(methyloxy)-6,7-dihydro-5H-indolo[2,1-a][2]benzazepine-10-carboxamide (230 mg, 0.34 mmol, 44%) as an orange-yellow solid. ¹HNMR (300 MHz, CDCl₃) δ 0.99-2.02 (m, 20H), 2.83-2.96 (m, 1H), 3.02 (s, 6H), 3.63-3.73 (m, 2H), 3.89 (s, 3H), 4.20-4.38 (m, 1H), 4.60-4.71 (m, 1H), 5.14-5.26 (m, 1H), 7.04 (dd, J=8.4, 2.6 Hz, 1H), 7.38 (d, J=8.4 Hz, 1H), 7.45 (br s, 1H), 7.55 (d, J=8.4 Hz, 1H), 7.79-7.97 (m, 2H). LCMS: m/e 667 (M–H)⁻, ret time 1.98 min, column A, 4 minute gradient.

Intermediate 6

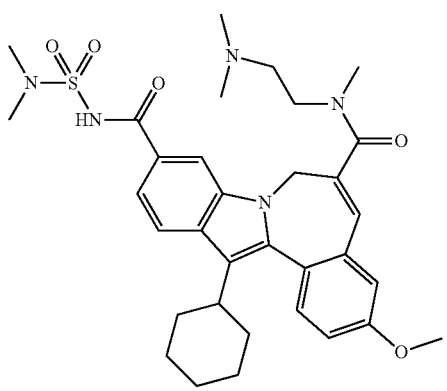

13-Cyclohexyl-N⁶-(2-(dimethylamino)ethyl)-N¹⁰-((dimethylamino)sulfonyl)-N⁶-methyl-3-(methyloxy)-7H-indolo[2,1-a][2]benzazepine-6,10-dicarboxamide. 7H-Indolo[2,1-a][2]benzazepine-6-carboxylic acid, 13-cyclohexyl-10-[[[(dimethylamino)sulfonyl]amino]carbonyl]-3-methoxy-, methyl ester (700 mg, 1.27 mmol) was dissolved into MeOH/THF (1:1, 14 mL) and treated with 1M aqueous NaOH (3 mL). The reaction mixture was stirred and heated at 80° C. with microwave irradiation for 15 min and cooled to rt. The clear solution was neutralized with 1M aqueous HCl (3 mL) and concentrated to remove organic solvents. The residue was stirred with H₂O (10 mL) for 1 h and the resultant solids were collected by filtration, washed with H₂O and dried under vacuum. To a solution of these solids, N¹,N¹,N²-trimethylethane-1,2-diamine (191 mg, 1.88 mmol) and triethylamine (0.700 mL) in DMF (5 mL) was added HATU (620 mg, 1.63 mmol). The reaction mixture was stirred at rt for 1 h, diluted with H₂O (25 mL) and 1M HCl (aq.) (5 mL) and stirred 20 min. The precipitates were collected by filtration, rinsed with H₂O and dried to yield impure product (960 mg) as a yellow powder. A crude sample (100 mg) of the impure product was dissolved into MeOH/DMF (3:1, 4 mL), filtered and purified by preparative HPLC (H₂O/CH₃CN with 10 mM NH₄OAc buffer) to yield 13-cyclohexyl-N⁶-(2-(dimethylamino)ethyl)-N¹⁰-((dimethylamino) sulfonyl)-3-methoxy-N⁶-methyl-7H-indolo[2,1-a][2]benzazepine-6,10-dicarboxamide (78 mg, 0.13 mmol, 95%) as a yellow solid. ¹HNMR (300 MHz, CD₃OD) δ 1.11-3.07 (m, 24H), 2.99 (s, 6H), 3.50-3.76 (m, 2H), 3.93 (s, 3H), 4.27-4.44 (m, 1H), 5.05-5.25 (m, 1H), 7.05 (s, 1H) 7.08 (d, J=2.6 Hz, 1H), 7.16 (dd, J=8.8, 2.6 Hz, 1H), 7.56 (d, J=8.4 Hz, 1H), 7.64 (dd, J=8.8, 1.5 Hz, 1H), 7.88 (d, J=8.4 Hz, 1H), 8.16 (br s, 1H). LCMS: m/e 620 (M−H)⁻, ret time 2.32 min, column A, 4 minute gradient.

Intermediate 7

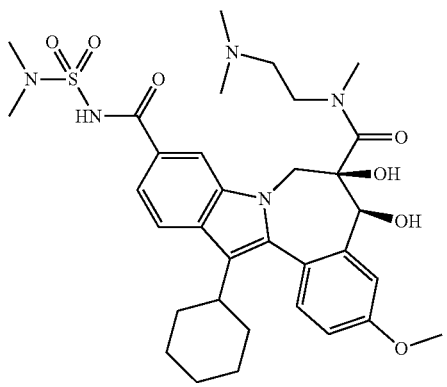

Diol, sulfamide, amide intermediate rac-(5R,6S)-13-Cyclohexyl-N⁶-(2-(dimethylamino)ethyl)-N¹⁰-((dimethylamino)sulfonyl)-5,6-dihydroxy-N⁶-methyl-3-(methyloxy)-6,7-dihydro-5H-indolo[2,1-a][2]benzazepine-6,10-dicarboxamide. To a solution of 13-cyclohexyl-N⁶-(2-(dimethylamino)ethyl)-N¹⁰-((dimethylamino)sulfonyl)-3-methoxy-N⁶-methyl-7H-indolo[2,1-a][2]benzazepine-6,10-dicarboxamide (200 mg, 0.32 mmol) and 4-methylmorpholine N-oxide (94 mg, 0.81 mmol) in THF/H₂O (10:1, 3.3 mL) was added OsO₄ (0.15 mL of a 2.5% w/w solution of OsO₄ in t-BuOH, 0.014 mmol). The reaction was stirred at rt for 2 h, additional OsO₄ (0.15 mL of a 2.5% w/w solution of OsO₄ in t-BuOH, 0.014 mmol) was added and the reaction was allowed to stir at rt overnight. The reaction mixture was quenched with sat. Na₂S₂O₃ (aq.) (~5 mL) and stirred 1 h. The layers were separated, and the aqueous layer was extracted with THF (2×4 mL). The combined organics were concentrated, slurried with water and the solids were collected by filtration to yield rac-(5R,6S)-13-cyclohexyl-N⁶-(2-(dimethylamino)ethyl)-N¹⁰-((dimethylamino)sulfonyl)-5,6-dihydroxy-N⁶-methyl-3-(methyloxy)-6,7-dihydro-5H-indolo[2,1-a][2]benzazepine-6,10-dicarboxamide (60 mg, 0.091 mmol, 28%) as a yellow solid, which was used without further purification. LCMS: m/e 654 (M−H)⁻, ret time 2.09 min, column A, 4 minute gradient.

Intermediate 8

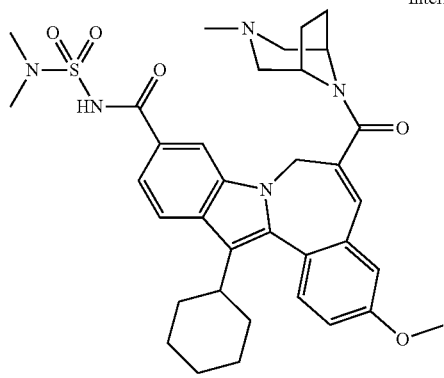

7H-Indolo[2,1-a][2]benzazepine-10-carboxamide, 13-cyclohexyl-N-[(dimethylamino)sulfonyl]-3-methoxy-6-[(3-methyl-3,8-diazabicyclo[3.2.1]oct-8-yl)carbonyl]. To a stirred solution of 13-cyclohexyl-N-[(dimethylamino)sulfonyl]-3-methoxy-7H-indolo[2,1-a][2]benzazepine-10-carboxamide-6-carboxylic acid (51 mg, 0.095 mmol), 3-methyl-3,8-diazabicyclo[3.2.1]octane dihydrochloride (34 mg, 0.17 mmol) and triethylamine (0.06 mL) in DMF (1.0 mL) was added HATU (50 mg, 0.13 mmol). The reaction mixture was stirred at rt for 2 h, diluted with MeOH (~1 mL), filtered and purified by preparative HPLC (CH₃CN/H₂O with 10 mM NH₄OAc) to yield 7H-indolo[2,1-a][2]benzazepine-10-carboxamide, 13-cyclohexyl-N-[(dimethylamino)sulfonyl]-3-methoxy-6-[(3-methyl-3,8-diazabicyclo[3.2.1]oct-8-yl)carbonyl] (52 mg, 0.08 mmol, 85%) as a yellow solid. ¹HNMR (300 MHz, CDCl₃) δ 8.31 (s, 1H), 7.83 (d, J=8.4 Hz, 1H), 7.59 (br d, J=8.4 Hz, 1H), 7.45 (d, J=8.8 Hz, 1H), 7.02 (dd, J=8.8, 2.6 Hz, 1H), 6.91-6.86 (m, 2H), 5.35-5.16 (m, 1H), 4.34-4.16 (m, 1H), 3.87 (s, 3H), 3.01 (s, 6H), 2.85-1.03 (m, 24H). LCMS: m/e 644 (M−H)⁻, ret time 2.89 min, column A, 4 minute gradient.

Intermediate 9

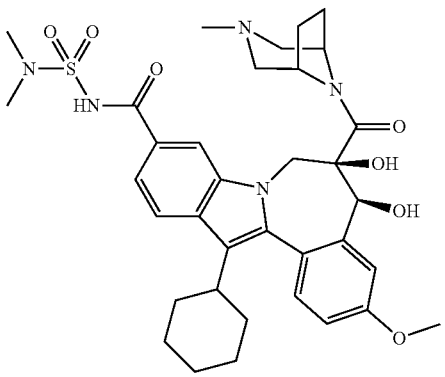

rac-(5R,6S)-13-Cyclohexyl-N-((dimethylamino)sulfonyl)-6-((3-methyl-3,8-diazabicyclo[3.2.1]oct-8-yl)carbonyl)-5,6-dihydroxy-3-(methyloxy)-6,7-dihydro-5H-indolo[2]benzazepine-10-carboxamid. To a solution of 7H-indolo[2,1-a][2]benzazepine-10-carboxamide, 13-cyclohexyl-N-[(dimethylamino)sulfonyl]-3-methoxy-6-[(3-methyl-3,8-diazabicyclo[3.2.1]oct-8-yl)carbonyl] (303 mg, 0.47 mmol) and 4-methylmorpholine N-oxide (138 mg, 1.2 mmol) in THF/H$_2$O (10:1, 4.4 mL) was added OsO$_4$ (0.45 mL of a 2.5% w/w solution of OsO$_4$ in t-BuOH, 0.04 mmol). The reaction was stirred at rt for 2 d, quenched with 1M Na$_2$S$_2$O$_3$ (aq.) (5 mL) and stirred 2 h. The solution was extracted with EtOAc (10 mL and then 5 mL). The combined organics were washed with 1M Na$_2$S$_2$O$_3$ (aq.) concentrated and purified by preparative HPLC (CH$_3$CN/H$_2$O with 10 mM NH$_4$OAc) to yield rac-(5R,6S)-13-cyclohexyl-N-((dimethylamino)sulfonyl)-6-((3-methyl-3,8-diazabicyclo[3.2.1]oct-8-yl)carbonyl)-5,6-dihydroxy-3-(methyloxy)-6,7-dihydro-5H-indolo[2,1-a][2]benzazepine-10-carboxamide (57 mg, 0.08 mmol, 18%) as a yellow solid, which was used without further purification. LCMS: m/e 680 (M+H)$^+$, ret time 1.66 min, column C, 2 minute gradient.

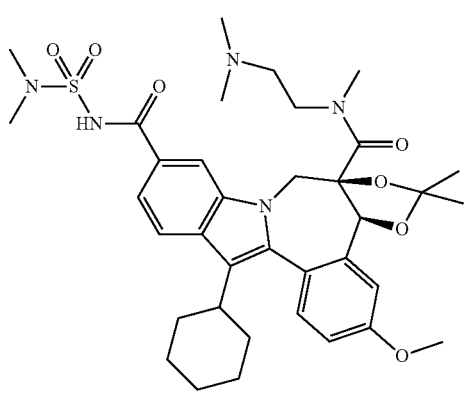

EXAMPLE 1 rac-(3aR,14bS)-10-Cyclohexyl-N$^{3a}$-(2-(dimethylamino)ethyl)-N$^7$-((dimethylamino)sulfonyl)-N$^{3a}$,2,2-trimethyl-13-(methyloxy)-4H-[1,3]dioxolo[4,5-d]indolo[2,1-a][2]benzazepine-3a,7(14bH)-dicarboxamide. 2-Methoxypropene (0.1 mL, 1.0 mmol) was added to a slurry of rac-(5R,6S)-13-cyclohexyl-N$^6$-(2-(dimethylamino)ethyl)-N$^{10}$-((dimethylamino)sulfonyl)-5,6-dihydroxy-N-methyl-3-(methyloxy)-6,7-dihydro-5H-indolo[2,1-a][2]benzazepine-6,10-dicarboxamide (30 mg, 0.045 mmol) in DCE (1 mL). p-TsOH monohydrate (1 mg, 0.005 mmol) was added and the reaction was stirred at rt overnight. Methylene chloride (1 mL) and additional p-TsOH monohydrate (10 mg, 0.05 mmol) were added and the reaction was stirred 2 h. The reaction was neutralized with 1N NaOH (aq) (1 mL) and the layers were separated. The organic layer was washed with brine, concentrated and purified by prep HPLC (CH$_3$CN/H$_2$O with 10 nM NH$_4$OAc) to yield rac-(3aR,14bS)-10-cyclohexyl-N$^{3a}$-(2-(dimethylamino)ethyl)-N$^7$-((dimethylamino)sulfonyl)-N$^{3a}$,2,2-trimethyl-13-(methyloxy)-4H-[1,3]dioxolo[4,5-d]indolo[2,1-a][2]benzazepine-3a,7(14bH)-dicarboxamide (16.7 mg, 0.024 mmol, 50%) as an off-white solid. $^1$HNMR (300 MHz, CD$_3$OD) δ 0.31 (s, 3H), 1.20-2.20 (m, 13H), 2.54 (s, 3H), 2.58 (s, 3H), 2.97 (s, 6H), 2.72-3.11 (m, 5H), 3.50-3.89 (m, 4H), 3.94 (s, 3H), 4.40-4.63 (m, 1H), 5.47-5.52 (m, 1H), 7.10-7.17 (m, 1H), 7.21-7.27 (m, 1H), 7.33-7.47 (m, H), 7.61-7.67 (m, 1H), 7.76-7.86 (m, 1H), 8.03-8.09 (m, 1H). LCMS: m/e 696 (M+H)$^+$, ret time 3.19 min, column B, 4 minute gradient.

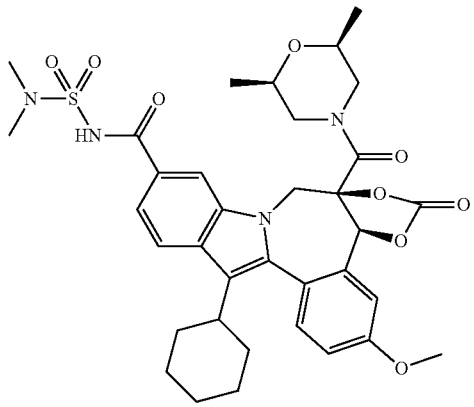

EXAMPLE 2 rac-(3aR,14bS)-10-Cyclohexyl-N-((dimethylamino)sulfonyl)-3a4(2R,6S)-2,6-dimethyl-4-morpholinyl)carbonyl)-13-(methyloxy)-2-oxo-3a,14b-dihydro-4H-[1,3]diaxolo[4,5-d]indolo[2,1-a][2]benzazepine-7-carboxamide. A solution of rac-(5R,6S)-13-cyclohexyl-N-((dimethylamino)sulfonyl)-6-(((2S,6R)-2,6-dimethyl-4-morpholinyl)carbonyl)-5,6-dihydroxy-3-(methyloxy)-6,7-dihydro-5H-indolo[2,1-a][2]benzazepine-10-carboxamide (35 mg, 0.052 mmol) and 1,1'-carbonyldiimidazole (58 mg, 0.36 mmol) in THF (2 mL) was sealed into a reaction vessel and heated at 75° C. with microwave irradiation for 20 min. (~50% conversion). Heating was continued at 80° C. for 40 min (~80% conversion). The reaction was cooled to rt, concentrated to dryness, dissolved into MeOH (~2 mL), filtered and purified by preparative HPLC (CH$_3$CN/H$_2$O with 10 mM NH$_4$OAc) to yield rac-(3aR,14bS)-10-cyclohexyl-N-((dimethylamino)sulfonyl)-3-(((2R,6S)-2,6-dimethyl-4-morpholinyl)carbonyl)-13-(methyloxy)-2-oxo-3a,14b-dihydro-4H-[1,3]dioxolo[4,5-d]indolo[2,1-a][2]benzazepine-7-carboxamide (20.6 mg, 0.030, 57%) as a white powder. $^1$HNMR (300 MHz, CDCl$_3$) δ 1.04-2.11 (m, 16H), 2.41-2.55 (m, 1H), 2.80-2.95 (m, 1H), 3.02 (s, 6H), 3.02-3.13 (m, 1H), 3.48-3.82 (m, 2H), 3.90 (s, 3H), 4.05-4.26 (m, 1H), 4.32-4.59 (m, 3H), 5.94 (d, J=14.3 Hz, 1H), 7.11 (br d, J=8.4 Hz, 1H), 7.20 (d, J=2.2 Hz, 1H), 7.30-7.39 (m, 1H), 7.43 (d, J=8.4 Hz, 1H), 7.78-7.91 (m, 2H). LCMS: m/e 693 (M−H)$^−$, ret time 2.77 min, column A, 4 minute gradient.

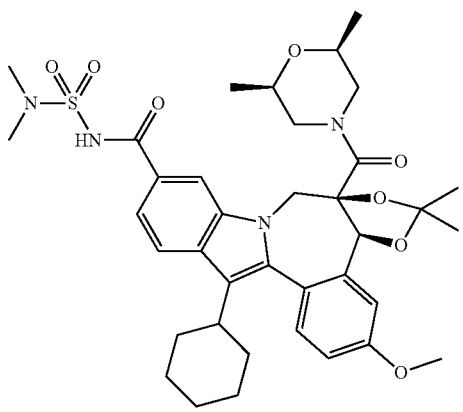

EXAMPLE 3 rac-(3aR,14bS)-10-Cyclohexyl-N-((dimethylamino)sulfonyl)-3a-(((2R,6S)-2,6-dimethyl-4-morpholinyl)carbonyl)-2,2-dimethyl-13-(methyloxy)-3a,14b-dihydro-4H-[1,3]dioxolo[4,5-d]indolo[2,1-a][2]benzazepine-7-carboxamide. To a solution of rac-(5R,6S)-13-cyclohexyl-N-((dimethylamino)sulfonyl)-6-(((2S,6R)-2,6-dimethyl-4-morpholinyl)carbonyl)-5,6-dihydroxy-3-(methyloxy)-6,7-dihydro-5H-indolo[2,1-a][2]benzazepine-10-carboxamide (60 mg, 0.090 mmol) in CH$_2$Cl$_2$ (3 mL) was added 2-methoxypropene (0.5 mL, 5.2 mmol) and TsOH.H$_2$O (50 mg, 0.26 mmol). The reaction solution was stirred at rt for 2 h, concentrated to dryness, dissolved into MeOH, filtered through an SPE column (C18, 500 mg, MeOH), concentrated and purified by preparative HPLC (CH$_3$CN/H$_2$O with 10 mM NH$_4$OAc) to yield rac-(3aR,14bS)-10-cyclohexyl-N-((dimethylamino)sulfonyl)-3a-(((2R,6S)-2,6-dimethyl-4-morpholinyl)carbonyl)-2,2-dimethyl-13-(methyloxy)-3a,14b-dihydro-4H-[1,3]dioxolo[2,1-a][2]benzazepine-7-carboxamide (15.5 mg, 0.022, 24%) as a light yellow solid. $^1$HNMR (300 MHz, CDCl$_3$) δ 0.28 (s, 3H), 0.88-2.12 (m, 19H), 2.36-2.49 (m, 1H), 2.85-3.01 (m, 2H), 3.03 (s, 6H), 3.48-3.80 (m, 2H), 3.88 (s, 3H), 3.89-4.04 (m, 1H), 4.22-4.50 (m, 2H), 4.76-4.96 (m, 1H), 5.52-5.59 (m, 1H), 7.01 (dd, J=8.4, 2.6 Hz, 1H), 7.20-7.33 (m, 2H), 7.37 (d, J=8.4 Hz, 1H), 7.78-7.91 (m, 2H). LCMS: m/e 707 (M−H)$^-$, ret time 3.26 min, column A, 4 minute gradient.

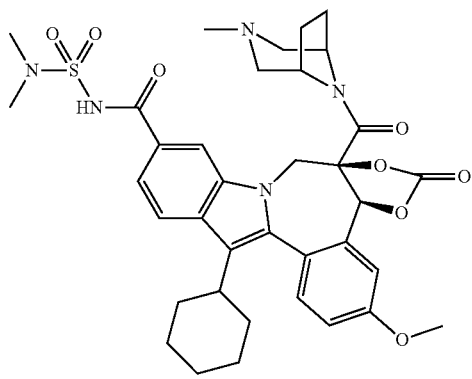

EXAMPLE 4 rac-(3aR,14bS)-10-Cyclohexyl-N-((dimethylamino)sulfonyl)-3a-((3-methyl-3,8-diazabicyclo[3.2.1]oct-8-yl)carbonyl)-13-(methyloxy)-2-oxo-3a,14b-dihydro-4H-[1,3]dioxolo[4,5-d]indolo[2,1-a][2]benzazepine-7-carboxamid. A solution of rac-(5R,6S)-13-cyclohexyl-N-((dimethylamino)sulfonyl)-6-((3-methyl-3,8-diazabicyclo[3.2.1]oct-8-yl)carbonyl)-5,6-dihydroxy-3-(methyloxy)-6,7-dihydro-5H-indolo[2,1-a][2]benzazepine-10-carboxamide (31 mg, 0.045 mmol) and 1,1'-carbonyldiimidazole (120 mg, 0.74 mmol) in TEA (0.1 mL) and THF (1 mL) was sealed into a reaction vessel and heated at 90° C. with microwave irradiation for 2 h. The reaction was cooled to rt, concentrated to dryness, dissolved into MeOH, filtered and purified by preparative HPLC (CH$_3$CN/H$_2$O with 10 mM NH$_4$OAc). The material containing the desired product was repurified by preparative HPLC (MeOH/H$_2$O with 10 mM TPA) to yield rac-(3aR,14bS)-10-cyclohexyl-N-((dimethylamino)sulfonyl)-3a-((3-methyl-3,8-diazabicyclo[3.2.1]oct-8-yl)carbonyl)-13-(methyloxy)-2-oxo-3a,14b-dihydro-4H-[1,3]dioxolo[4,5-d]indolo[2,1-a][2]benzazepine-7-carboxamide (9.5 mg, 0.013 mmol, 30%) as a white solid. $^1$HNMR (300 MHz, CD$_3$OD) δ 1.20-2.33 (m, 14H), 2.87-3.02 (m, 5H), 3.04 (s, 6H), 3.35-4.52 (m, 3H), 3.96 (s, 3H), 4.23 (br d, J=14.6, 1H), 4.75 (br d, J=14.6, 1H), 4.95 (br s, 1H), 5.16 (br s, 1H), 6.11 (br s, 1H), 7.26-7.32 (m, 2H), 7.55 (d, J=8.8 Hz, 1H), 7.63 (dd, J=8.4, 1.5 Hz, 1H), 7.94 (d, J=8.4 Hz, 1H), 7.99 (br s, 1H). LCMS: m/e 706 (M+H)$^+$, ret time 1.56 min, column C, 2 minute gradient.

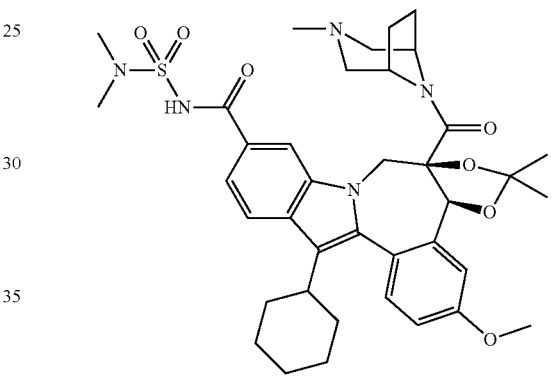

EXAMPLE 5 rac-(3aR,4bS)-10-Cyclohexyl-N-((dimethylamino)sulfonyl)-2,2-dimethyl-3a-((3-methyl-3,8-diazabicyclo[3.2.1]oct-8-yl)carbonyl)-13-(methyloxy)-3a,14b-dihydro-4H-[1,3]dioxolo[4,5-d]indolo[2,1-a][2]benzazepine-7-carboxamid. To a solution of rac-(5R,6S)-13-cyclohexyl-N-((dimethylamino)sulfonyl)-6-((3-methyl-3,8-diazabicyclo[3.2.1]oct-8-yl)carbonyl)-5,6-dihydroxy-3-(methyloxy)-6,7-dihydro-5H-indolo[2,1-a][2]benzazepine-10-carboxamide (42 mg, 0,062 mmol) and 2-methoxypropene (0.5 mL, 5.2 mmol) in CH$_2$Cl$_2$ (0.5 mL) was added and TsOH.H$_2$O (5 mg. 0.026 mmol). The reaction solution was stirred at rt overnight, concentrated to dryness, dissolved into MeOH, filtered, and purified by preparative HPLC (CH$_3$CN/H$_2$O with 10 mM NH$_4$OAc) to yield rac-(3aR,14bS)-10-cyclohexyl-N-((dimethylamino)sulfonyl)-2,2-dimethyl-3a-((3-methyl-3,8-diazabicyclo[3.2.1]oct-8-yl)carbonyl)-13-(methyloxy)-3a,14b-dihydro-4H-[1,3]dioxolo[4,5-d]indolo[2,1-a][2]benzazepine-7-carboxamide (6.7 mg, 0.1 mmol, 15%) as an off-white solid. $^1$HNMR (300 MHz, CD$_3$OD) δ 0.33 (s, 3H), 1.19-2.54 (m, 22H), 2.65-2.78 (m, 0.5H), 2.90-3.02 (m, 2H), 3.03 (s, 6H), 3.16-3.28 (m, 0.5H), 3.91 (d, J=15.0 Hz, 0.5H), 3.94 (s, 3H), 4.05 (d, J=15.0 Hz, 0.5H), 4.34 (d, J=15.0 Hz, 0.5H), 4.58 (d, J=15.0 Hz, 0.5H), 4.66-4.74 (m, 1H), 5.15-5.22 (m, 0.5H), 5.45-5.59 (m, 1.5H), 7.15 (dd, J=8.4, 2.6 Hz, 1H), 7.22-7.29 (m, 1H), 7.45 (dd, J=8.4 Hz, 1H), 7.59 (dd, J=8.4, 1.8 Hz, 1H), 7.86-7.93 (m, 2H). LCMS: m/e 718 (M−H)$^-$, ret time 1.60 min, column F, 2 minute gradient.

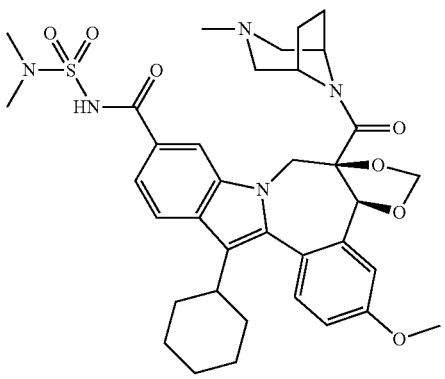

EXAMPLE 6 rac-(3aR,14bS)-10-Cyclohexyl-N-((dimethylamino)sulfonyl)-3a-((3-methyl-3,8-diazabicyclo[3.2.1]oct-8-yl)carbonyl)-13-(methyloxy)-3a,14b-dihydro-4H-[1,3]dioxolo[4,5-d]indolo[2,1-a][2]benzazepine-7-carboxamid. To a solution of rac-(5R,6S)-13-cyclohexyl-N-((dimethylamino)sulfonyl)-6-((3-methyl-3,8-diazabicyclo[3.2.1]oct-8-yl)carbonyl)-5,6-dihydroxy-3-(methyloxy)-6,7-dihydro-5H-indolo[2,1-a][2]benzazepine-10-carboxamide (47 mg, 0.069 mmol) in $CH_2Cl_2$ (1 mL) and $CH_2Br_2$ (1 mL) was added $nBu_4N^+I^-$ (16 mg, 0.043 mmol) and 5.5N NaOH (aq) (0.6 mL). The reaction solution was stirred at rt overnight, concentrated to remove $CH_2Cl_2$, diluted with $CH_2Br_2$ (1 mL) and stirred at 50° C. in a sealed vessel overnight. The crude reaction mixture was concentrated to dryness and purified by preparative HPLC (MeOH/$H_2O$ with 10 mM TFA) to yield rac-(3aR,14bS)-10-cyclohexyl-N-((dimethylamino)sulfonyl)-3a-((3-methyl-3,8-diazabicyclo[3.2.1]oct-8-yl)carbonyl)-13-(methyloxy)-3a,14b-dihydro-4H-[1,3]dioxolo[4,5-d]indolo[2,1-a][2]benzazepine-7-carboxamide (14.5 mg, 0.21 mmol, 30%) as a bright yellow solid. $^1$HNMR (300 MHz, $CD_3OD$) δ 1.21-2.39 (m, 16H), 2.74, (s, 3H), 2.84-2.97 (m, 2H), 3.02 (s, 6H), 3.44-3.54 (m, 1H), 3.87 (d, J=15.0, 1H), 3.95 (s, 3H), 4.08-4.27 (m, 2H), 5.23-5.29 (m, 2H), 5.43-5.46 (m, 1H), 5.93 (d, J=7.7 Hz, 1H), 7.11-7.19 (m, 2H), 7.47 (d, J=8.1 Hz, 1H), 7.58 (dd, J=8.4, 1 Hz, 1H), 7.94 (d, J=8.4 Hz, 1H), 7.99 (br s, 1H). LCMS: m/e 692 (M+H)$^+$, ret time 1.89 min, column C, 2 minute gradient.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of formula I

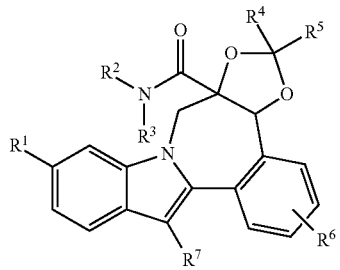

where:
$R^1$ is $CO_2R^8$ or $CONR^9R^{10}$;
$R^2$ is hydrogen, alkyl, aminoalkyl, alkylaminoalkyl, or dialkylaminoalkyl;
$R^3$ is hydrogen, alkyl, aminoalkyl, alkylaminoalkyl, or dialkylaminoalkyl;
or $NR^2R^3$ taken together is azetidinyl, pyrrolidinyl, piperidinyl, piperazinyl, N-(alkyl)piperazinyl, morpholinyl, thiomorpholinyl, homopiperidinyl, or homomorpholinyl, and is substituted with 0-3 alkyl substituents;
or $NR^2R^3$ taken together is

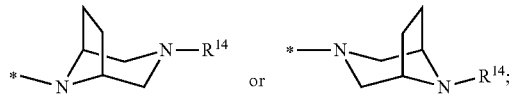

$R^4$ is hydrogen or alkyl;
$R^5$ is hydrogen or alkyl;
or $R^4$ and $R^5$ taken together is oxo;
$R^6$ is hydrogen, halo, alkyl, alkenyl, hydroxy, benzyloxy, or alkoxy;
$R^7$ is cycloalkyl;
$R^8$ is hydrogen or alkyl;
$R^9$ is hydrogen, alkyl, alkylSO$_2$, cycloalkylSO$_2$, haloalkylSO$_2$, $(R^{11})(R^{12})NSO_2$, or $(R^{13})SO_2$;
$R^{10}$ is hydrogen or alkyl;
$R^{11}$ is hydrogen or alkyl;
$R^{12}$ is hydrogen or alkyl;
$R^{13}$ is azetidinyl, pyrrolidinyl, piperidinyl, piperazinyl, N-(alkyl)piperazinyl, morpholinyl, thiomorpholinyl, homopiperidinyl, or homomorpholinyl; and
$R^{14}$ is hydrogen, alkyl, cycloalkyl, (cycloalkyl)alkyl, alkylcarbonyl, cycloalkylcarbonyl, haloalkylcarbonyl, alkoxycarbonyl, alkylSO$_2$, cycloalkylSO$_2$, haloalkylSO$_2$, aminocarbonyl, (alkylamino)carbonyl, (dialkylamino)carbonyl, benzyl, benzyloxycarbonyl, or pyridinyl;
or a pharmaceutically acceptable salt thereof.

2. A compound of claim 1 where $R^1$ is $CONR^9R^{10}$; $R^2$ is dialkylaminoalkyl; $R^3$ is alkyl; or $NR^2R^3$ taken together is morpholinyl substituted with 2 alkyl substituents or $NR^2R^3$ taken together is

$R^4$ is hydrogen or alkyl; $R^5$ is hydrogen or alkyl; or $R^4$ and $R^5$ taken together is oxo; $R^6$ is alkoxy; $R^7$ is cycloalkyl; $R^9$ is $(R^{11})(R^{12})NSO_2$; $R^{11}$ is alkyl; $R^{12}$ is alkyl; and $R^{14}$ is alkyl; or a pharmaceutically acceptable salt thereof.

3. A compound of claim 2 where $R^1$ is $CONHSO_2NMe_2$; $R^2$ is dimethylaminoethyl; $R^3$ is methyl; or $NR^2R^3$ taken together is 3,5-dimethylmorpholinyl or $NR^2R^3$ taken together is 3-methyl-3,8-diazabicyclo[3.2.1]oct-8-yl; $R^4$ is hydrogen or methyl; $R^5$ is hydrogen or methyl; or $R^4$ and $R^5$ taken together is oxo; $R^6$ is methoxy; $R^7$ is cyclohexyl; or a pharmaceutically acceptable salt thereof.

4. A compound of claim 1 where $R^1$ is $CONR^9R^{10}$; $R^9$ is alkylSO$_2$, cycloalkylSO$_2$, haloalkylSO$_2$, $(R^{11})(R^{12})NSO_2$, or $(R^{13})SO_2$; and $R^{10}$ is hydrogen.

5. A compound of claim 1 where $R^6$ is hydrogen.

6. A compound of claim 1 where $R^6$ is methoxy.

7. A compound of claim 1 where $R^7$ is cyclohexyl.

8. A compound of claim 1 where $R^9$ is $(R^{11})(R^{12})NSO_2$ or $(R^{13})SO_2$.

9. A compound of claim 1 with the following stereochemistry

10. A compound of claim 1 selected from the group consisting of

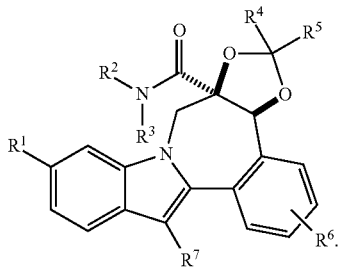

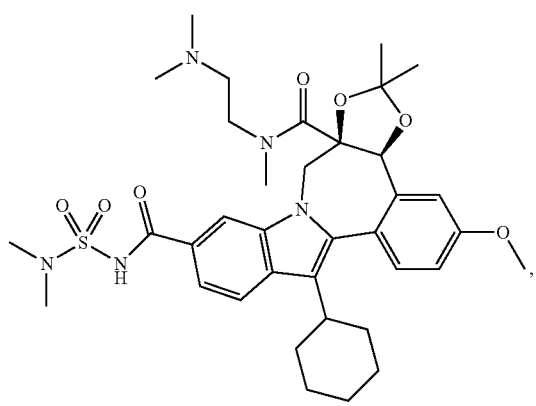

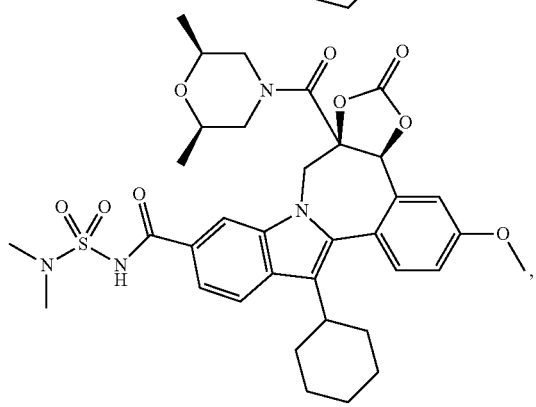

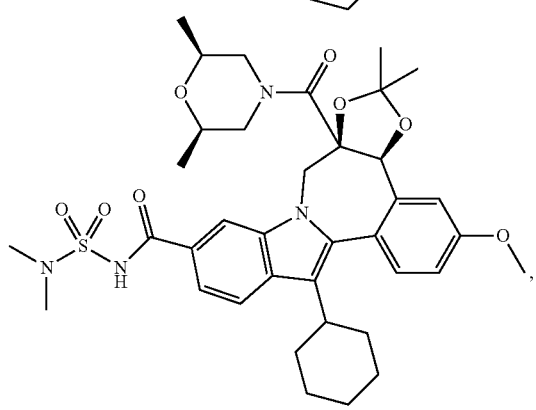

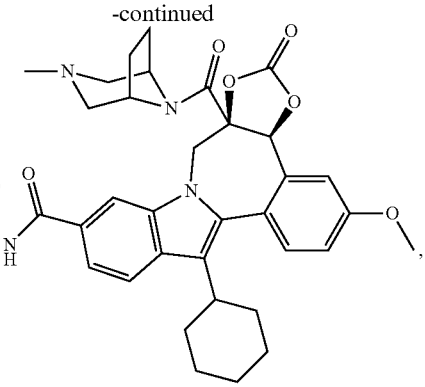

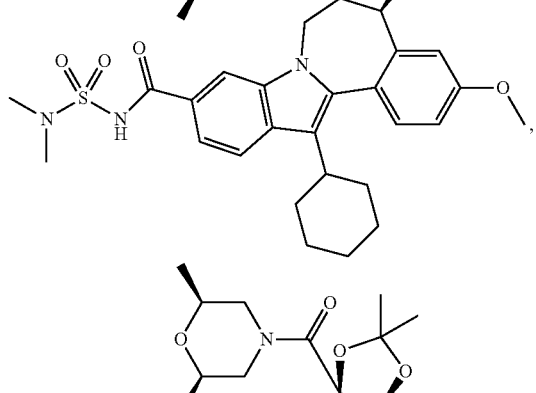

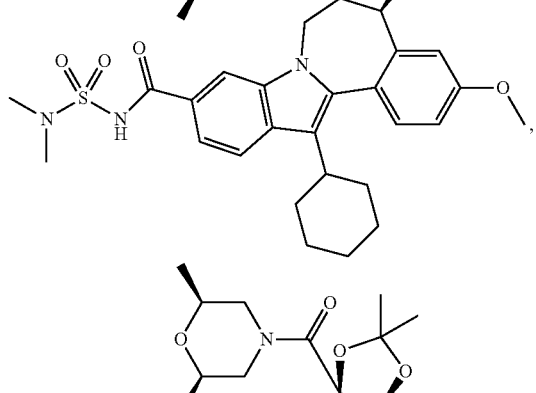

or a pharmaceutically acceptable salt thereof.

11. A composition comprising a compound of claim 1, or a pharmaceutically acceptable salt thereof, and a pharmaceutically acceptable carrier.

12. A method of treating hepatitis C infection comprising administering a therapeutically effective amount of a compound of claim 1 to a patient.

* * * * *

UNITED STATES PATENT AND TRADEMARK OFFICE
CERTIFICATE OF CORRECTION

PATENT NO. : 8,138,171 B2
APPLICATION NO. : 12/922927
DATED : March 20, 2012
INVENTOR(S) : John A. Bender et al.

It is certified that error appears in the above-identified patent and that said Letters Patent is hereby corrected as shown below:

In the Claims:

Claim 1:

Column 30, line 34, change "alkylSO$_z$," to -- alkylSO$_2$, --.

Signed and Sealed this
Eleventh Day of March, 2014

Michelle K. Lee
*Deputy Director of the United States Patent and Trademark Office*